(12) United States Patent
Von Zabern et al.

(10) Patent No.: US 9,427,240 B2
(45) Date of Patent: Aug. 30, 2016

(54) SYSTEM AND METHOD FOR PERFORMING MEASURABLE AND CONTROLED OSTEOTOMY

(71) Applicants: Robert Von Zabern, Rvierside, CA (US); Jeff Von Zabern, Riverside, CA (US)

(72) Inventors: Robert Von Zabern, Rvierside, CA (US); Jeff Von Zabern, Riverside, CA (US)

(73) Assignee: Von Zabern Surgical, Riverside, CA (US)

( * ) Notice: Subject to any disclaimer, the term of this patent is extended or adjusted under 35 U.S.C. 154(b) by 444 days.

(21) Appl. No.: 13/815,997

(22) Filed: Mar. 21, 2013

(65) Prior Publication Data
US 2014/0288562 A1   Sep. 25, 2014

(51) Int. Cl.
*A61B 17/15* (2006.01)
*A61B 17/16* (2006.01)
*A61D 1/00* (2006.01)

(52) U.S. Cl.
CPC ......... *A61B 17/151* (2013.01); *A61B 17/1637* (2013.01); *A61D 1/00* (2013.01)

(58) Field of Classification Search
CPC .. A61B 17/15; A61B 17/151; A61B 17/152; A61B 17/154; A61B 17/157
See application file for complete search history.

(56) References Cited

U.S. PATENT DOCUMENTS

| | | | | |
|---|---|---|---|---|
| 1,208,150 A | * | 12/1916 | Hall | 83/767 |
| 3,872,761 A | * | 3/1975 | Gutowski et al. | 83/767 |
| 4,565,191 A | * | 1/1986 | Slocum | 606/87 |
| 4,574,794 A | * | 3/1986 | Cooke et al. | 606/88 |
| 4,627,425 A | * | 12/1986 | Reese | 606/87 |
| 4,638,700 A | * | 1/1987 | Fushiya et al. | 83/468.3 |
| 4,677,973 A | * | 7/1987 | Slocum | 606/60 |
| 4,738,253 A | * | 4/1988 | Buechel et al. | 606/80 |
| 4,750,481 A | * | 6/1988 | Reese | 606/87 |
| 4,952,213 A | * | 8/1990 | Bowman et al. | 606/79 |
| 4,979,949 A | * | 12/1990 | Matsen et al. | 606/53 |
| 5,171,244 A | * | 12/1992 | Caspari et al. | 606/88 |
| 5,275,603 A | * | 1/1994 | Ferrante et al. | 606/86 R |
| 5,358,504 A | * | 10/1994 | Paley et al. | 606/56 |
| 5,376,093 A | * | 12/1994 | Newman | 606/88 |
| 5,514,143 A | * | 5/1996 | Bonutti et al. | 606/86 R |
| 5,645,548 A | * | 7/1997 | Augsburger | 606/87 |
| 5,669,914 A | * | 9/1997 | Eckhoff | 606/88 |
| 5,681,316 A | * | 10/1997 | DeOrio et al. | 606/88 |
| 5,788,700 A | * | 8/1998 | Morawa et al. | 606/88 |
| 5,810,827 A | * | 9/1998 | Haines et al. | 606/80 |
| 5,911,724 A | * | 6/1999 | Wehrli | 606/88 |
| 5,928,234 A | * | 7/1999 | Manspeizer | 606/54 |
| 6,024,746 A | * | 2/2000 | Katz | 606/88 |
| 6,030,391 A | * | 2/2000 | Brainard et al. | 606/87 |
| 6,077,270 A | * | 6/2000 | Katz | 606/88 |
| 6,235,029 B1 | * | 5/2001 | Faccioli et al. | 606/54 |
| 6,423,061 B1 | * | 7/2002 | Bryant | 606/57 |
| 6,428,540 B1 | * | 8/2002 | Claes et al. | 606/53 |
| 7,182,766 B1 | * | 2/2007 | Mogul | 606/87 |
| 7,364,581 B2 | * | 4/2008 | Michalowicz | 606/87 |
| 7,507,242 B2 | * | 3/2009 | Triplett et al. | 606/87 |
| 7,763,026 B2 | * | 7/2010 | Egger et al. | 606/87 |
| 7,909,831 B2 | * | 3/2011 | Axelson et al. | 606/87 |
| 7,935,119 B2 | * | 5/2011 | Ammann et al. | 606/87 |

(Continued)

*Primary Examiner* — Christian Sevilla
*Assistant Examiner* — Eric S Gibson

(57) ABSTRACT

Providing a system for performing a CORA based leveling osteotomy. The system enables a uniform precise osteotomy and mechanical rotation of the proximal tibia concentric to the osteotomy and a means for fixing an osteotomy plate or brace while the system reduces the osteotomy through compression.

1 Claim, 2 Drawing Sheets

(56) References Cited

U.S. PATENT DOCUMENTS

| | | | |
|---|---|---|---|
| 8,192,441 B2 * | 6/2012 | Collazo | 606/87 |
| 8,241,292 B2 * | 8/2012 | Collazo | 606/87 |
| 8,632,547 B2 * | 1/2014 | Maxson et al. | 606/88 |
| 8,764,760 B2 * | 7/2014 | Metzger et al. | 606/88 |
| 8,771,279 B2 * | 7/2014 | Philippon et al. | 606/87 |
| 8,926,618 B2 * | 1/2015 | Collazo | 606/87 |
| 9,078,669 B2 * | 7/2015 | Dower | |
| 2001/0001121 A1 * | 5/2001 | Lombardo et al. | 606/89 |
| 2002/0165552 A1 * | 11/2002 | Duffner | 606/87 |
| 2002/0198531 A1 * | 12/2002 | Millard et al. | 606/87 |
| 2004/0153066 A1 * | 8/2004 | Coon et al. | 606/54 |
| 2005/0021039 A1 * | 1/2005 | Cusick et al. | 606/88 |
| 2005/0209605 A1 * | 9/2005 | Grimm et al. | 606/96 |
| 2005/0273112 A1 * | 12/2005 | McNamara | 606/87 |
| 2006/0052791 A1 * | 3/2006 | Hagen et al. | 606/86 |
| 2006/0122616 A1 * | 6/2006 | Bennett et al. | 606/87 |
| 2007/0100346 A1 * | 5/2007 | Wyss et al. | 606/87 |
| 2007/0173849 A1 * | 7/2007 | Claypool et al. | 606/87 |
| 2007/0173850 A1 * | 7/2007 | Rangaiah et al. | 606/87 |
| 2007/0173851 A1 * | 7/2007 | McMillen et al. | 606/87 |
| 2008/0015607 A1 * | 1/2008 | D'Alessio et al. | 606/87 |
| 2008/0183176 A1 * | 7/2008 | Canonaco et al. | 606/87 |
| 2008/0195099 A1 * | 8/2008 | Minas | 606/70 |
| 2008/0195109 A1 * | 8/2008 | Hunter et al. | 606/87 |
| 2008/0195110 A1 * | 8/2008 | Plassy et al. | 606/88 |
| 2009/0043309 A1 * | 2/2009 | Rasmussen | 606/88 |
| 2009/0043310 A1 * | 2/2009 | Rasmussen | 606/88 |
| 2009/0112212 A1 * | 4/2009 | Murray et al. | 606/87 |
| 2009/0234360 A1 * | 9/2009 | Alexander | 606/88 |
| 2009/0287216 A1 * | 11/2009 | Warkentine et al. | 606/87 |
| 2010/0191243 A1 * | 7/2010 | Horan et al. | 606/87 |
| 2010/0191244 A1 * | 7/2010 | White et al. | 606/88 |
| 2011/0009868 A1 * | 1/2011 | Sato | 606/87 |
| 2011/0106091 A1 * | 5/2011 | Fisher et al. | 606/88 |
| 2011/0106092 A1 * | 5/2011 | Fisher et al. | 606/88 |
| 2011/0208200 A1 * | 8/2011 | Keffer | A61B 17/157 606/87 |
| 2012/0130383 A1 * | 5/2012 | Budoff | 606/87 |
| 2013/0096563 A1 * | 4/2013 | Meade et al. | 606/88 |
| 2013/0190766 A1 * | 7/2013 | Harris et al. | 606/87 |
| 2013/0211411 A1 * | 8/2013 | Tuke et al. | 606/88 |
| 2014/0046331 A1 * | 2/2014 | Amos et al. | 606/80 |
| 2014/0066720 A1 * | 3/2014 | Wilkinson et al. | 600/235 |
| 2014/0288562 A1 * | 9/2014 | Von Zabern et al. | 606/88 |
| 2015/0157339 A1 * | 6/2015 | McGinley et al. | |
| 2015/0157340 A1 * | 6/2015 | McGinley et al. | |

* cited by examiner

SYSTEM AND METHOD FOR PERFORMING MEASURABLE AND CONTROLED OSTEOTOMY

FIELD OF INVENTION

The present invention relates to a system and method that is used to perform an osteotomy to repair long bone alignment defects and improve joint function.

BACKGROUND OF THE INVENTION

Injuries to joints causing lameness commonly occur as a result of an injury or rupture of ligaments. The lameness often worsens as cartilage erosion and degenerative joint disease occurs. An example of common joint injury in human knees relate to injury or rupture of the anterior cruciate ligament (ACL) causing offset angulation of the knee joint. A similar injury in four legged animals occurs in the cranial cruciate ligament of the stifle joint. One preferred embodiment for practicing this invention can be disclosed in relation with a veterinary surgery for the stifle joint.

The cranial cruciate ligament in the stifle restrains a sliding motion of the tibia when exercising the stifle joint. A distressed or ruptured cranial cruciate ligament enables misalignment of the tibia relative to the femur thereby causing further damage of the stifle joint. Tibia plateau leveling osteotomy is a common method of treatment and taught by Barclay Slocum in U.S. Pat. No. 4,677,973 entitled "PROXIMAL, TIBIAL OSTEOTOMY FOR LEVELING A TIBIA PLATEAU" whereby an osteotomy of the proximal tibial is performed to level the tibia plateau.

Tibia plateau leveling osteotomy is not based on the mechanical or anatomic center of rotation of angulation and therefore results in caudal displacement of the weight bearing axis and a focal increase in joint force. Tibia plateau leveling osteotomy also causes caudal thrust resulting in further damage to the stifle.

Drawbacks relating to tibia plateau leveling osteotomy are addressed by a procedure known as the Center of Rotation of Angulation (CORA) based leveling osteotomy. Center of Rotation of Angulation (CORA) is the point at which proximal and distal axis intersect. When performed correctly the CORA based leveling osteotomy relieves the drawbacks related to the tibia plateau leveling osteotomy while changing the slope of the tibia plateau in the stifle joint. The CORA based leveling osteotomy additionally preserves the proximal tibial epiphysis for application of ancillary stabilizing procedures. Furthermore post operatively the CORA based leveling osteotomy establishes a preferred and stabilizing ninety degree patella tendon to tibia plateau slope angle.

Furthermore, CORA based leveling osteotomy as known in the art preserves the proximal tibial epiphysis which allows for additional stabilizing procedures, normalizing cranial thrust and producing a desired tibia plateau slope angle.

A drawback relating to the CORA based leveling osteotomy is realized during surgery due to its complexity. More specifically obtaining the desired rotation of the proximal tibia segment is challenged by forces generated by connected muscle and ligaments. Inaccurate rotation of the proximal tibia segment can further damage the stifle. These risks results in slow adoption of the CORA based leveling osteotomy.

SUMMARY OF THE INVENTION

The present invention relates generally, to a system for performing CORA based leveling osteotomy (CBLO) whereby a single system enables control of the osteotomy. The invention will be disclosed in the context of performing a CBLO on a canine but it should be understood that the invention is useable in various osteotomies and on various animals including human beings.

One more particularly innovative aspect of the present invention relates to the ability of the system to provide a fixation means which fixes the system to the tibia enabling a control means that mechanically rotates the proximal tibia in relation to the distal tibia and a measuring means together enabling precise measurable rotation of the proximal tibia relative to the distal tibia.

Another particularly important aspect of the invention relates to a system for use in an osteotomy whereby the system provides a central pivot pin for the saw blade enabling a uniform osteotomy through the tibia. A uniform osteotomy through the tibia enables a more successful reduction of osteotomy promoting quicker healing.

Another particularly important aspect of the invention is that the system provides a method of performing an osteotomy that is in the exact desired preoperatively planned location.

Another particularly important aspect of the invention is realized when reducing the osteotomy whereby the system provides a method for applying uniform hands-free rigidly maintained compression of the osteotomy that is easily altered but rigidly maintained during the placement of an osteotomy plate or implants.

Another particularly important aspect of the invention is realized when considering that a single system enables the measurable control and a connected relational geometric plane in which each step of the procedure can reference removing the need to speculate angles and degrees of rotation as well as eliminating the use of external charts, calculations, bone marking techniques, inexact rotation, placement of temporary fixation hardware, difficulties in visualization due to hemorrhage and regional soft tissues, or inadvertent changes in orientation that are not desired.

These key innovative aspects of the invention which directly address the potential errors of a traditional osteotomy or CBLO reduce the complexity of the procedure enabling a more rapid adoption.

BRIEF DESCRIPTION OF THE DRAWINGS

In the accompanying drawings that form a part of the specification and that are to be read in conjunction therewith and in which like reference numerals are used to indicate like parts in the various views.

DETAILED DESCRIPTION OF THE DRAWINGS

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

A portion of the invention may be described herein in terms of steps. It should be appreciated that such steps may be realized by alternative order.

The overall purpose of the system described herein is to provide a means of measurable control and accuracy when performing an osteotomy, precise angular correction within the stifle joint and hands-free rigidly maintained compression of the osteotomy during the placement of an osteotomy plate and screws. The advantages of the system can be fully realized when performing a CBLO.

Figure 1:
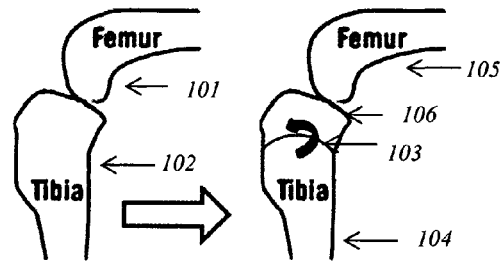
FIG. 1 is a diagram representing the basic theory of a CBLO osteotomy on a hind leg.

Performing a CBLO of which basics are represented in FIG. 1 or a surgical procedure with like characteristics it is desirable to have control over the proximal tibia (106) and the distal tibia (104). Such goal is reached through attachment of the system to the tibia (101) such that post osteotomy (103) utilizing CORA the system is attached to the proximal tibia (106) and the distal tibia (104) and is configured to enable measurable mechanical rotation of the proximal tibia (106) in relation to the distal tibia.

Figure 2:
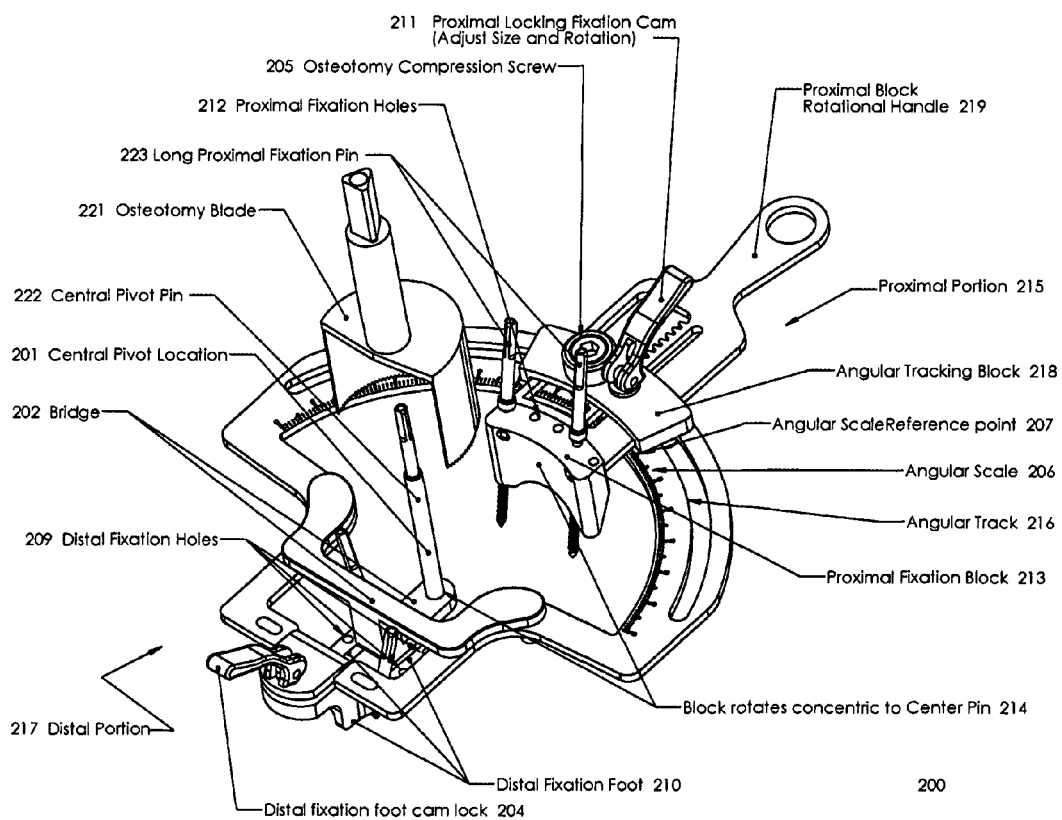
FIG. 2 is a diagram illustrating one embodiment of the system in an isometric view.
Figure 3:
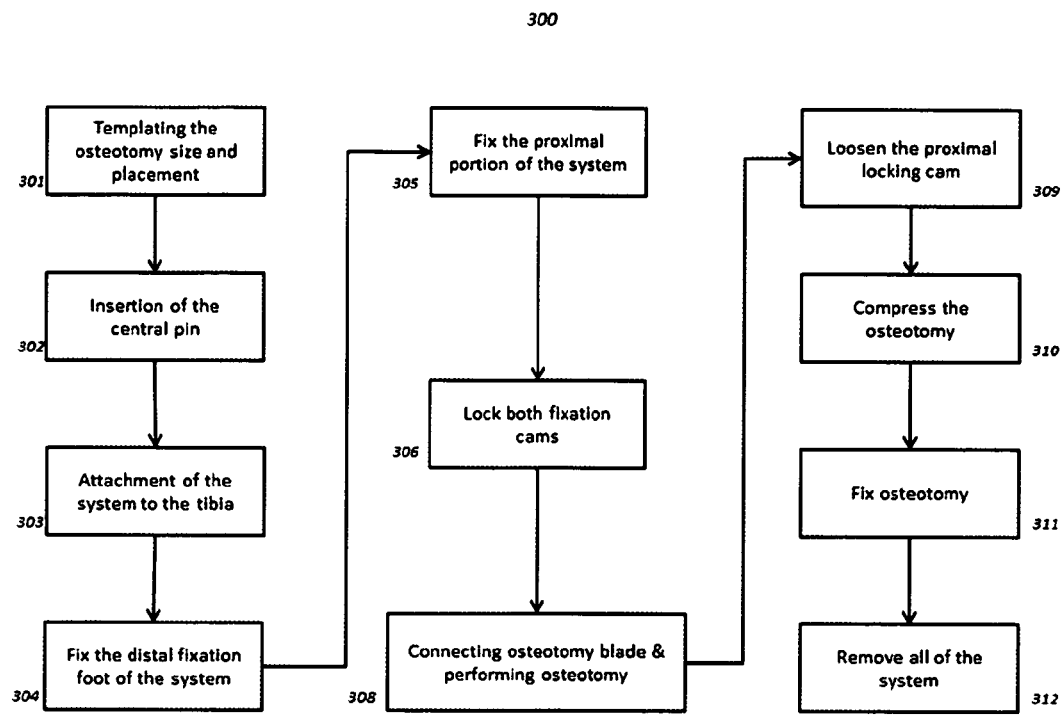
FIG. 3 is a flowchart illustrating the steps while using the system in a CBLO.
Figure 4:
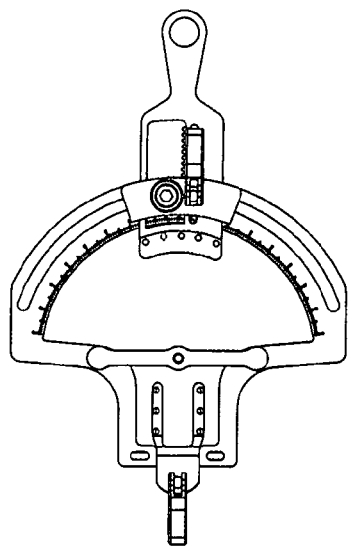
FIG. 4 is a diagram illustrating one embodiment of the system in a top view.

As represented in FIG. 2 and FIG. 3, the system (FIG. 2:200) and parts thereof represent only particular innovative steps relating to the system as to be performed in a CBLO (FIG. 3:300).

Prior to surgery the surgeon will use a template (FIG. 3:301) or related instrument to determine the best blade size to produce a curvilinear osteotomy (FIG. 1:103) suitable for the presented tibia. The surgeon will also identify the CORA through various imaging techniques and tools and establish the preferred location of the osteotomy (FIG. 1:103) on the tibia (FIG. 1:102).

Upon surgical exposure of the stifle and the tibia, the surgeon will drive a central pin through the central pivot location (FIG. 2:201) fixing the bridge (FIG. 2:202), which includes a means of attaching to the system (FIG. 2:200) to the bridge (FIG. 2:202). The central pivot lactation (FIG. 2:201) and related bridge (FIG. 2:202) provides a central reference for the system (FIG. 2:200) and the osteotomy saw blade.

The surgeon then attaches the system (FIG. 2:200) to the tibia (FIG. 3:303) by way of attaching to the bridge (FIG. 2:202) whereby the elongated portion of the system (FIG. 2:200) resides in parallel with the elongated portion of the tibia.

Fixation of the distal fixation foot (FIG. 2:210) of the system (FIG. 2:200) is the next step (FIG. 3:304). This is performed by driving a plurality of fixation pins, which may be self-tapping threaded pins, through the plurality of distal fixation holes (FIG. 2:209) that comprise the distal fixation foot (FIG. 2:210) thereby fixing the distal fixation foot (FIG. 2:210) to the tibia. To ensure torqueing of the system (FIG. 2:200) or torqueing of the tibia does not occur, forces maybe relieved by the distal fixation foot cam lock (FIG. 2:204) such that the distal fixation foot (FIG. 2:210) smartly resides on the tibia as to evenly secure the system (FIG. 2:200) in a balanced and aligned manner. When engaged, the distal fixation foot cam lock (FIG. 2:204) restricts movement of the distal fixation foot (FIG. 2:210) in relation to the system (FIG. 2:200).

Fixing the proximal portion (215) of the system (FIG. 2:215); (FIG. 3:305) includes releasing the proximal locking fixation CAM (FIG. 2:211), which enables travel of the rotational proximal block rotation handle (FIG. 2:219) through the angular tracking block (FIG. 2:218) by means of the osteotomy compression screw (FIG. 2:205). The proximal block rotational handle (FIG. 2:219) is operably attached to the proximal fixation block (FIG. 2:213) whereby travel of the proximal block rotational handle (FIG. 2:219) enables the proximal fixation block (FIG. 2:213), which includes a concave end for mating with the convex tibia, moves adjacent to the tibia in the elongated direction to locate a preferred fixation point. Upon placement of the proximal fixation block (FIG. 2:213) on a preferred fixation point a plurality of long fixation pins FIG. 2:223, which may be self-tapping threaded pins, are driven into the tibia through the plurality of proximal fixation holes (FIG. 2: 212) thereby fixing the proximal fixation block (FIG. 2:213) to the tibia.

The proximal locking fixation CAM (FIG. 2:211) and the distal fixation foot CAM lock (FIG. 2:204), must now be locked (FIG. 3:306) thereby firmly fixing the system to the tibia.

The osteotomy can now be performed by means of operably connecting (FIG. 3:308) a cannulated osteotomy blade (FIG. 2:221) over the central pivot pin (FIG. 2:222) that passes through and is stabilized by the bridge (FIG. 2:202) such that unwanted movement of the saw will translate into relating movement of the tibia even while cutting thereby ensuring a uniform curvilinear cut. The osteotomy results in the segmentation of the tibia forming a proximal tibia (FIG. 1:106) and a distal tibia (FIG. 1:104).

Upon completing the osteotomy and removing the cannulated osteotomy blade from the central pivot pin (FIG. 2:222), loosening of the proximal locking fixation CAM (FIG. 2:211); (FIG. 3:309) enables the angular tracking block (FIG. 2:218) to travel in an arching formation along the angular track (FIG. 2:216) whereby the angular track (FIG. 2:216) includes an angular scale (FIG. 2:206) representing the degrees of rotation. The angular scale may also comprise of a marking means to identify the initial point of travel. Travel of the angular tracking block (FIG. 2:218) in an arching formation along the angular track (FIG. 2:216) enables the measurable rotation of the proximal tibia in relation to the distal tibia precisely concentric to the osteotomy.

Upon obtaining the desired rotation of proximal tibia, the system (FIG. 2:200) provides the ability to reduce the osteotomy (FIG. 3:310) by compression. Compression is enabled by way of rotating the compression screw (FIG. 2:205) where rotation in one direction moves the proximal fixation block (FIG. 2:213) by operable connection to the proximal block rotational handle (FIG. 2:219) towards the distal portion (217) of the system thereby causing the contact and compression of the proximal tibia to the distal tibia.

Upon reaching the desired compression and reduction of the osteotomy, an osteotomy plate is fixed (FIG. 3:311) by means of driving a plurality of pins or screws through the plurality holes located on the osteotomy plate while the system provides compression.

The particular steps to be performed in a CBLO (FIG. 3:300) as outlined herein are meant to represent the key innovation of the system. The steps are not meant to represent a complete account of the steps performed of an osteotomy or more specifically all steps related to a CBLO.

What is claimed is:

1. A system for performing a CBLO, the system comprising:
   a central pivot pin, configured to be inserted at a central pivot location of a tibia;
   a bridge, fixed to the central pivot pin;
   a cannulated saw blade, fixed to the central pivot pin, for performing a complete curvilinear osteotomy of the tibia thereby segmenting the tibia into a proximal tibia section and a distal tibia section;

a distal fixation foot configured to be fixed to the distal tibia section;

a proximal fixation block configured to be fixed to the proximal tibia section and connected to a proximal block rotational handle through an angular tracking block;

an angular track having an arching formation, and configured to be attached to the proximal tibia section;

the angular tracking block being movably connected to the angular track;

an angular scale representing degrees of rotation; and whereby the angular track is configured to be connected to the proximal tibia section to enable travel of the angular tracking block along the angular track for a mechanical control of the proximal tibia section while rotating the proximal tibia section in relation to the distal tibia section.

\* \* \* \* \*